(12) United States Patent
Bezemer et al.

(10) Patent No.: US 6,730,721 B2
(45) Date of Patent: May 4, 2004

(54) MOLDING OF A POLYMER

(75) Inventors: Jeroen Mattijs Bezemer, Utrecht (NL); Joost Robert de Wijn, Nijmegen (NL); Jan Nieuwenhuis, Gorinchem (NL)

(73) Assignee: IsoTis N.V., Bilthoven (NL)

( * ) Notice: Subject to any disclaimer, the term of this patent is extended or adjusted under 35 U.S.C. 154(b) by 61 days.

(21) Appl. No.: 10/047,427

(22) Filed: Jan. 15, 2002

(65) Prior Publication Data

US 2002/0128378 A1 Sep. 12, 2002

Related U.S. Application Data

(63) Continuation of application No. PCT/NL00/00554, filed on Aug. 4, 2000.

(51) Int. Cl.⁷ .................................................. C08K 5/00
(52) U.S. Cl. ...................................... 523/508; 523/511
(58) Field of Search .................................. 523/508, 511

(56) References Cited

U.S. PATENT DOCUMENTS 4,102,859 A * 7/1978 Eimers et al. .............. 524/109

FOREIGN PATENT DOCUMENTS

| EP | 0318788 A | 6/1989 |
|----|-----------|--------|
| EP | 0891783 A | 1/1999 |
| GB | 1403210 A | 8/1975 |
| GB | 1404340 A | 8/1975 |

* cited by examiner

*Primary Examiner*—Kriellion A. Sanders
(74) *Attorney, Agent, or Firm*—Banner & Witcoff, Ltd.

(57) ABSTRACT

The invention relates to a process for molding a copolymer of a polyalkylene glycol terephthalate and an aromatic ester, comprising the steps of: a) preparing a solution of the copolymer in a suitable first solvent; and b) forming a gel of the solution.

12 Claims, No Drawings

MOLDING OF A POLYMER

This application is a continuation of prior international application No. PCT/NL00/00554, filed Aug. 4, 2000; which claims priority from European Patent Application No. EP 99202599.9, filed Aug. 6, 1999.

The invention relates to a process for molding a polymer. More in particular, the invention relates to a process for molding a copolymer of a polyalkylene glycol terephthalate and an aromatic ester.

Copolymers of a polyalkylene glycol terephthalate and an aromatic esters have been found to possess highly favorable properties, such as biodegradability and biocompatibility. For these reasons, they are finding application in tissue engineering applications, such as in the function of scaffolds for seeding cells of different types. Particularly, copolymers of polyethylene glycol terephthalate (PEGT) and polybutylene terephthalate, which are known under the name of Polyactive®, have been found to give promising results in this regard.

In order for the copolymers to be suitable for use in these applications, it is necessary that their shape can be efficiently controlled. Solid bodies of different shapes can be formed of these copolymers, and in fact of polymers in general, in several ways. Well-known examples include injection molding and extrusion.

Most methods for giving a desired shape to a polymer material comprise the step of preparing a melt of the polymer so that it can be formed into the desired shape. Once formed into the desired shape, it is hardened or cured. In order to prepare the melt it is usually necessary to work at the very high temperatures required for obtaining a melt.

Under certain circumstances, it is desired to be able to produce a solid body of a polymer without subjecting it to the high temperatures required for obtaining a melt. Often the thermal strain imposed on a polymeric material during extrusion is undesired. Particular (partial) oxidation of the polymeric material is to be avoided. It is accordingly an object of the present invention to provide a method of molding a copolymer of a polyalkylene glycol terephthalate and an aromatic ester which leads in an efficient manner to a solid body of a desired shape under mild conditions.

Further, in particular in view of the above referred to applications of the copolymers it is often desired to be able to incorporate (bioactive) additives in the solid bodies to be formed. For instance, the presence of growth factors may be very much desired in order to enhance cell growth or differentiation. As many of these bioactive additives are very sensitive compounds the need for working under mild conditions becomes even more important. It is thus a further object of the invention to provide a method for molding a copolymer of a polyalkylene glycol terephthalate and an aromatic ester under mild conditions, which method can conveniently be adapted in order to incorporate additives into the solid body to be formed.

Surprisingly, it has now been found that the properties of copolymers of a polyalkylene glycol terephthalate and an aromatic ester make it possible to produce solid bodies of them in a gel molding process. Accordingly, the invention relates to a process for molding a copolymer of a polyalkylene glycol terephthalate and an aromatic ester, comprising the steps of:

a) preparing a solution of the copolymer in as suitable first solvent; and b) forming a gel of the solution.

The present process does not involve the preparation of a melt of the copolymer. It has been found that, in accordance with the invention, the copolymer may be molded into any desired shape under very mild conditions. The solvents used can advantageously be recovered and recycled.

The copolymer which is formed into a solid body according to the invention, is a copolymer of a polyalkylene glycol terephthalate and an aromatic polyester. Preferably, the copolymer comprises 20–90 wt. %, more preferably 40–70 wt. % of the polyalkylene glycol terephthalate, and 80–10 wt. %, more preferably 60–30 wt. % of the aromatic polyester. A preferred type of copolymers according to the invention is formed by the group of block copolymers.

The polyalkylene glycol terephthalate may have a weight average molecular weight of about 150 to about 4000. Preferably, the polyalkylene glycol terephthalate has a weight average molecular weight of 200 to 1500. The aromatic polyester Preferably has a weight average molecular weight of from 200 to 5000, more preferably from 250 to 4000. The weight average molecular weight of the copolymer preferably lies between 10,000 and 300,000, more preferably between 40,000 and 120,000.

The weight average molecular weight may suitably be determined by gel permeation chromatography (GPC). This technique, which is known per se, may for instance be performed using chloroform as a solvent and polystyrene as external standard. Alternatively, a measure for the weight average molecular weight may be obtained by using viscometry (see NEN-EN-ISO 1628-1). This technique may for instance be performed at 25° C. using chloroform as a solvent. Preferably, the intrinsic viscosity of the copolymer lies between 0.2289 and 1.3282 dL/g, which corresponds to a weight average molecular weight between 10,000 and 200,000. Likewise, the more preferred ranges for the, weight average molecular weight measured by GPC mentioned above can also be expressed in terms of the intrinsic viscosity.

In a preferred embodiment, the polyalkylene glycol terephthalate component has units of the formula —OLO—CO—Q—CO—, wherein O represents oxygen, C represents carbon, L is a divalent organic radical remaining after removal of terminal hydroxyl groups from a poly(oxyalkylene)glycol, and Q is a divalent organic radical.

Preferred polyalkylene glycol terephthalates are chosen from the group of polyethylene glycol terephzalate, polypropylene glycol terephthalate, and polybutylene glycol terephthalate and copolymers thereof, such as poloxamers. A highly preferred polyalkylene glycol terephthalate is polyethylene glycol terephthalate.

The terms alkylene and polyalkylene generally refer to any isomeric structure, i.e. propylene comprises both 1,2-propylene and 1,3-propylene, butylene comprises 1,2-butylene, 1,3-butylene, 2,3-butylene, 1,2-isobutylene, 1,3-isobutylene and 1,4-isobutylene (tetramethylene) and similarly for higher alkylene homologues. The polyalkylene glycol terephthalate component is preferably terminated with a dicarboxylic acid residue —CO—Q—CO—, if necessary to provide a coupling to the polyester component. Group Q may be an aromatic group having the same definition as R, or may be an aliphatic group such as ethylene, propylene, butylene and the like.

The polyester component preferably has units —O—E—O—CO—R—CO—, wherein O represents oxygen, C represents carbon, E is a substituted or unsubstituted alkylene or oxydialkylene radical having from 2 to 8 carbon atoms, and R is a substituted or unsubstituted divalent aromatic radical.

In a preferred embodiment, the polyester is chosen from the group of polyethylene terephthalate, polypropylene terephthalate, and polybutylene terephthalate. A highly preferred polyester is polybutylene terephthalate.

The preparation of the copolymer will now be explained by way of example for a polyethylene glycol terephthalate/polybutylene terephthalate copolymer. Based on this description, the skilled person will be able to prepare any desired copolymer within the above described class. An alternative manner for preparing polyalkylene glycol terephthalate/polyester copolymers is disclosed in U.S. Pat. No. 3,908,201.

A polyethylene glycol terephthalate/polybutylene terephthalate copolymer may be synthesized from a mixture of dimethyl terephthalate, butanediol (in excess), polyethylene glycol, an antioxidant and a catalyst. The mixture is placed in a reaction vessel and heated to about 180° C., and methanol is distilled as transesterification proceeds. During the transesterification, the ester bond with methyl is replaced with an ester bond with butylene and/or the polyethyene glycol.

In accordance with the invention, the copolymer is first dissolved in a suitable solvent, by which is meant that a substantially homogeneous, one phase mixture is prepared of the copolymer and said suitable solvent. Depending on the nature of the copolymer and the solvent, it may be necessary to work at elevated temperature in order to dissolve the copolymer. However, the temperature required for this step will always be low in comparison with the temperature that would be needed to prepare a melt of the copolymer. Thus, the present process allows the molding of the copolymer under mild conditions. Suitable temperatures for preparing the solution will be below the boiling temperature of the solvent, preferably between 20° C. and 200° C., more preferably between 30° C. and 100° C.

The solvent to be used should be suitable for dissolving the copolymer. Also, it should be possible to form the solution containing the polymer into a gel. Solvents that have been found to be useful for this purpose are relatively polar organic solvents. Preferred examples ate solvents with a relatively high boiling point, facilitating dissolution of the copolymer. Particularly preferred are N-methylpyrrolidone, 1,4-dioxane, 1,3-dioxane, and combinations thereof. N-methylpyrrolidone is most preferred.

It is preferred that a relatively concentrated solution of the copolymer is prepared in order to facilitate the formation of the gel. Preferably, the solution is prepared using such relative amounts of copolymer and solvent, that the solution comprises between 5 and 90 wt. %, preferably between 50 and 80 wt. %, of the copolymer, based on the weight of the solution.

The solution of the copolymer is subsequently transformed into a gel. In this regard, the term 'gel' is intended to refer to a colloidal solution. Upon the transformation of the solution of the copolymer into the gel the viscosity will increase markedly. Preferably, the viscosity is so high that a moldable, dough-like solid is obtained. The gel formation may be accomplished by slightly cooling the solution. In case the solution is prepared at elevated temperatures, it will generally suffice to allow the solution to cool to room temperature. Generally, it is desired that the cooling will proceed faster than the gelification.

Before the solution is gelified, it is possible to mix additives into the solution, which will be incorporated into the gel, and consequently also into the solid body to be formed. As at this stage the solution will still have a relatively low viscosity, it is possible to homogeneously distribute the additives throughout the solution. Accordingly, the additives will be present throughout the solid body to be formed, in homogeneous fashion. In other words, the copolymer forms a matrix in which the additive or additives are homogeneously distributed.

The additives may vary widely in nature; in principle any type of additive may be incorporated as long as its nature or used amount does not obstruct with the gel-forming capacity of the copolymer. Depending on the envisaged application of the solid body of the copolymer, the additive may be chosen from the group of biologically active agents. As the copolymer is biodegradable in vivo the additives will be released to the surroundings of the solid body in a controlled manner. This behavior of the copolymer has previously been described in EP-A-0 830 859. These additives may be added to the solution in amounts ranging from 0 to 50 wt. %, preferably from 1 to 20 wt. %.

The term "biologically active agent", as used herein, means an agent which provides a therapeutic or prophylactic effect. Such agents include, but are not limited to, antimicrobial agents (including antibacterial and anti-fungal agents), anti-viral agents, anti-tumor agents, hormones immunogenic agents, growth factors, lipids, and lipopolysaccharides.

Biologically active agents which may be incorporated include, but are not limited to, non-peptide, non-protein small-sized drugs. They have a molecular weight which in general is less than 1500, and in particular less than 500. A second important group of biologically active agents are biologically active peptides and proteins.

Examples of non-peptide, non-protein small-sized drugs which may be incorporated include, but are not limited to, the following:

1. Anti-tumor agents: altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin.
2. Antimicrobial agents
    2.1 Antibiotics
    Penicillins: ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin Cephalosporins: cefaclor, cephalothin, cefadroxil, cephapirin, cefamandole, cephradine, cefatrizine, cefsulodine, cefazolin, cefLazidim, ceforanide, ceftriaxon, cefoxitin, cefuroxime, cephacetrile, latamoxef, cephalexin
    Aminoglycosides: amikacin, neomycin, dibekacyn, kanamycin, gentamycin, netilmycin, kanamycin, tobramycin Macrolides: amphotericin B, novobiocin, bacitracin, nystatin, clindamycin, polymyxins, colistin, rovamycin, erythromycin, spectinomycin, lincomycin, vancomycin Tetracyclines: chlortetracycline, oxytetracycline, demeclocycline, rolitetracycline, doxycycline, tetracycline, minocycline
    Other antibiotics: chloramphenicol, rifamycin, rifampicin, thiamphenicol
    2.2 Chemotherapeutic agents
    Sulfonamides: sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole, trimethoprim with sulfamethoxazole or sulfametrole
Urinary tract antiseptics: methanamine, quinolones (norfloxacin, cinoxacin), nalidixic acid, nitro-compounds (nitrofurantoine, nifurtoinol), oxolinic acid
Anaerobic infections: metronidazole
3. Drugs for tuberculosis: aminosalicyclic acid, isoniazide, cycloserine, rifampicine, ethamburol, tiocarlide, ethionamide, viomycin
4. Drugs for leprosy: amithiozone, rifampicine, clofazimine, sodium sulfoxone, diaminodiphenylsulfone (DDS, dapsone)
5. Antifungal agents: amphotericin B, ketoconazole, clotrimazole, miconazole, econazole, natamycin, flucytosine, nystatine, griseofulvin
6. Antiviral agents: aciclovir, idoxuridine, amantidine, methisazone, cytarabine, vidarabine, ganciclovir
7. Chemotherapy of amebiasis: chloroquine, iodoquinol, clioquinol, metronidazole, dehydroemetine, paromomycin, diloxanide, furoatetinidazole, emetine
8. Anti-malarial agents: chloroquine, pyrimethamine, hydroxychloroquine, quinine, mefloquine, sulfadoxine/pyrimethamine, pentamidine, sodium suramin, primaquine, trimethoprim, proguanil
9. Anti-helminthiasis agents: antimony potassium tartrate, niridazole, antimony sodium dimercaptosuccinate, oxamniquine, bephenium, piperazine, dichiorophen, praziquantel, diethylcarbamazine, pyrantel parmoate, hycanthone, pyrivium pamoate, levamisole, stibophen, mebendazole, tetramisole, metrifonate, thiobendazole, niclosamide
10. Anti-inflammatory agents: acetylsalicyclic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen, tolmetin
11. Anti-gout agents: colchicine, allopurinol
12. Centrally acting (opoid) analgesics: alfentanil, methadone, bezitramide, morphine, buprenorfine, nicomorphine, butorfanol, pentazocine, codeine, pethidine, dextromoramide, piritranide, dextropropoxyphene, sufentanil, fentanyl
13. Local anesthetics: articaine, mepivacaine, bupivacaine, prilocaine, etidocaine, procaine, lidocaine, tetracaine
14. Drugs for Parkinson's disease: amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide, trihexyphenidyl
15. Centrally active muscle relaxants: baclofen, carisoprodol, chlormezanone, chlorzoxazone, cyclobenzaprine, dantrolene, diazepam, febarbamate, mefenoxalone, mephenesin, metoxalone, methocarbamol, tolperisone
16. Hormones and hormone antagonistics
    16.1 Corticosteroids
        16.1.1 Mineralocorticosteroids: cortisol, desoxycorticosterone, fluorohydrocortisone
        16.1.2 Glucocorticosteroids: beclomethasone, betamethasone, cortisone, dexamethasone, fluocinolone, fluocinonide, fluocortolone, fluorometholone, fluoprednisolone, flurandrenolide, halcinonide, hydrocortisone, medrysone, methylprednisolone, paramethasone, prednisolone, prednisone, triamcinolone(acetonide)
    16.2 Androgens
        16.2.1 Androgenic steroids used in therapy: danazole, fluoxymesterone, mesterolone, methyltestosterone, testosterone and salts thereof
        16.2.2 Anabolic steroids used in therapy: calusterone, nandrolone and salts thereof, dromostanolone, oxandrolone, ethylestrenol; oxymetholone, methandriol, stanozolol methandrostenolone, testolactone
        16.2.3 Antiandrogens: cyproterone acetate
    16.3 Estrogens
        16.3.1 Estrogenic steroids used in therapy: diethylstilbestrol, estradiol, estriol, ethinylestradiol, mestranol, quinestrol
        16.3.2 Anti-estrogens: chlorotrianisene, clomiphene, ethamoxytriphetol, nafoxidine, tamoxifen
    16.4 Progestins: allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, progesterone
17. Thyroid drugs
    17.1 Thyroid drugs used in therapy: levothyronine, liothyronine
    17.2 Anti-thyroid drugs used in therapy: carbimazole, methimazole, methylthiouracil, propylthiouracil When a non-peptide, non-protein, small-sized drug, such as those described above, is to be incorporated, the polyalkylene glycol terephthalate component of the copolymer preferably has a molecular weight of from about 200 to 400. Also, the polyalkylene glycol terephthalate component is present in the copolymer in an amount of from 20 wt. % to 90 wt. % of the weight of the copolymer, preferably from about 40 wt. % to about 70 wt. % of the weight of the copolymer. In general, the aromatic polyester is present in the copolymer in an amount of from 10 wt. % to 80 wt. % of the copolymer, preferably in an amount of from about 30 wt. % to about 60 wt. % of the copolymer.

When a hydrophobic small-sized drug, such as, for example, a steroid hormone is incorporated, preferably at least one hydrophobic antioxidant is present. Hydrophobic antioxidants which may be employed include, but are not limited to, tocopherols, such as α-tocopherol, β-tocopherol, γ-tocopherol, δ-tocopherol, ε-tocopherol, $\xi_1$-tocopherol, $\xi_2$-tocopherol, and η-tocopherol; and 1-ascorbic acid 6-palmitate. Such hydrophobic anzioxidants retard the degradation of the copolymer and retard the release of the biologically active agent. Thus, the use of a hydrophobic or lipophilic antioxidant is applicable particularly to the formation of matrices which include drugs which tend to be released quickly from the microspheres, such as, for example, small drug molecules having a molecular weight less than 500. The at least one hydrophobic antioxidant may be present in the matrix in an amount of from about 0.1 wt. % to about 10 wt. % of the total weight of the matrix, preferably from about 0.5 wt. % to about 2 wt. %.

When the matrix includes a hydrophilic small-sized drug, such as an aminoglycoside, the matrix may also include, in addition to the hydrophobic antioxidant, a hydrophobic molecule such as cholesterol, ergosterol, lithocholic acid, cholic acid, dinosterol, betuline, or oleanolic acid, which may be employed in order to retard the release rate of the agent from the copolymer matrix. Such hydrophobic molecules prevent water penetration into the matrix, but do not compromise the degradability of the matrix. In addition, such molecules have melting points from 150° C. to 200° C. or decreases the matrix diffusion coefficient for the biologically active agent, such as small drug molecule, to be released. Thus, such hydrophobic molecules provide for a more sustained release of a biologically active agent from the matrix. The at least one hydrophobic molecule may be present in the matrix in an amount of from about 0.1 wt. % to about 20 wt. %, preferably from 1.0 wt.% to 5.0 wt. %.

If it is desired to increase the hydrophilicity of the polymer, and thereby increase the degradation rate and drug releasing rate of the copolymer, the copolymer may be modified by partially replacing the aromatic moiety with an aliphatic moiety such as succinate and/or by replacing partially the alkylene with dioxyethylene. For example, terephthalate can be replaced by succinate in an amount of from about 0.1 mole % to about 20 mole %, preferably from about 0.1 mole % to about 5 mole %, by partially replacing dimethyl terephthalate as a starting component with dimethyl succinate. As another example, butylene is replaced with oxydiethylene in an amount of from about 0.1 mole % to about 20 mole %, preferably from about 0.5 mole % to about 2 mole %, by replacing 1,4-butanediol with dimethyleneglycol as a starting component.

Examples of peptides or proteins which may advantageously be contained in the matrix include, but are not limited to, immunogenic peptides or immunogenic proteins, which include, but are not limited to, the following:

Growth factors: bone morphogenetic proteins, transforming growth factors, fibroblast growth factors, epidermal growth factors, etc.

Toxins: diphtheria toxin, tetanus toxin Viral surface antigens or parts of viruses: adenoviruses, Epstein-Barr Virus, Hepatitis A Virus, Hepatitis B Virus, Herpes viruses, HIV-1, HIV-2, HTLV-III, Influenza viruses, Japanese encephalitis virus, Measles virus, Papilloma viruses, Paramyxoviruses, Polio Virus, Rabies, Virus, Rubella Virus, Vaccinia (Smallpox) viruses, Yellow Fever Virus Bacterial surface antigens or parts of bacteria: *Bordetella pertussis, Helicobacter pylori, Clostridium tetani, Corynebacterium diphtheria, Escherichia coli, Haemophilus influenza, Klebsiella species, Legionella pneumophila, Mycobacterium bovis, Mycobacterium leprae, Mycrobacterium tuberculosis, Neisseria gonorrhoeae, Neisseria meningitidis, Proteus species, Pseudomonas aeruginosa, Salmonella species, Shigella species, Staphylococcus aureus, Streptococcus pyogenes, Vibrio cholera, Yersinia pestis*

Surface antigens of parasites causing disease or portions of parasites: *Plasmodium vivax*—malaria, *Plasmodium falciparum*—malaria, *Plasmodium ovale— malaria, Plasmodium malariae—malaria, Leishmania tropica—leishmaniasis, Leishmania donovani, leishmaniasis, Leishmania branziliensis—leishmaniasis, Trypanosoma rhodescense*—sleeping sickness, *Trypanosoma gambiense*—sleeping sickness, *Trypanosoma cruzi*—Chagas' disease, *Schistosoma mansoni—schistosomiasis, Schistosomoma haematobium—schistomiasis, Schistosoma japonicum—shichtomiasis, Trichinella spiralis— trichinosis, Stronglyloides duodenale*—hookworm, *Ancyclostoma duodenale*—hookworm, *Necator americanus*—hookworm, *Wucheria bancrofti—filariasis, Brugia malaya —filariasis, Loa loa—filariasis, Dipetalonema perstaris—filariasis, Dracuncula medinensis— filariasis, Onchocerca volvulus—filariasis* Immunoglobulins: IgG, IgA, IgM, *Antirabies immunoglobulin, Antivaccinia immunoglobulin* Antitoxins: *Botulinum antitoxin, diphtheria antitoxin, gas gangrene* antitoxin, *tetanus antitoxin.*

Other peptides or proteins which may be encapsulated include, but are not limited to, antigens which elicit an immune response against Foot and Mouth Disease, hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII and Antithrombin III. Examples of other proteins or peptides which may be encapsulated include, but are not limited to, albumin, atrial natriuretic factor, renin, superoxide dismutase, $\alpha_1$-antitrypsin, lung surfactant proteins, bacitracin, bestatin, cydosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, des-enkephalin-$\alpha$-endorphin, gonadotropin releasing hormone, leuprolide, $\alpha$-MSH, and metkephamid. It is to be understood, however, that the scope of the present invention is not limited to any specific peptides or proteins.

It has also been found to incorporate additives of a more constructive nature into the solid body of the copolymer. Thus, the invention also provides a method for preparing composite materials at room temperature. Particular suitable additives in this regard are ceramic materials. Preferred examples of such ceramic materials are calcium phosphates those which are both sufficiently biocompatible and sufficiently biodegradable to be used as an implant in living tissue can be used. Preferred calcium phosphates are octacalcium phosphate, apatites, such as hydroxyapatite and carbonate apatite, whitlockites, such as $\alpha$-tricalcium phosphate and $\beta$-tricalcium phosphate, and combinations thereof. These ceramics may be added to the solution in amounts ranging from 0 to 75 wt. %, preferably from 40 to 60 wt. %.

As has been mentioned above, the solution, optionally comprising one or more of the above additives, is formed into a gel, which may conveniently be done by slightly cooling the solution. In case the solution is prepared at elevated temperature, as is preferred, it will usually suffice to allow the solution to cool to room temperature.

The thus obtained gel may subsequently be formed into a solid body by removing the suitable first solvent. Depending on the nature of the suitable first solvent, one manner of doing this is by freezedrying. A different way of removing the first suitable solvent is by placing the gel in a second suitable solvent. The nature of the second suitable solvent is to be chosen such that the first suitable solvent dissolves readily in it. Also, it is important that the copolymer itself does not dissolve in the second suitable solvent. Accordingly, by placing the gel in the second suitable solvent, the first solvent present in the gel will migrate into the second solvent, leaving a solid body of the copolymer. Examples of suitable solvents include water and aqueous solutions, such as body fluids, ethanol and isopropanol.

As the second solvent can be composed of body fluids, it is also possible to use the gel as such and inject it into a patient's body. The first solvent will migrate into the body fluids and be removed by the patient's circulatory systems. Of course, care should be taken that the first solvent used is biocompatible. Upon the migration of the first solvent, the gel will harden and be transformed into a solid body. The use of the injectable gel is highly advantageous in many applications in for instance orthopedic or corrective surgery. Due to the advantageous properties of the copolymer, it is envisaged that the gel may be injected into bone defects or used in meniscus repair.

It is further possible to use the gel in a spinning or injection molding apparatus, for instance to produce fibers of the material.

It has been found that any additive, such as a biologically active agent which was incorporated into the gel will substantially entirely remain in the copolymer matrix during the transformation of the gel into a solid body if so desired. Of course, in certain cases the additive will not completely dissolve in the gel, and a two phase system is obtained. Advantageously, it has been found that the solid body that is formed upon immersing into the second solution will have substantially the same shape as the gel itself. Although a small reduction in size may be encountered, the skilled person will have no problems adjusting the dimensions of the gel to these circumstances.

The amount of the second solvent to be used can be easily optimized by the person skilled in the art. Generally, sufficient solvent should be used for the gel to be immersed in. Also, there should be a sufficient amount of the second solvent for the first solvent present in the gel to essentially completely dissolve in said second solvent. Typical amounts of the second solvent will be at least 300 vol. %, with respect to the volume of the gel.

The solid body formed may have various applications. It has been found to be particular useful to function in the field of surgical devices and aids, such as bone filler cement. In addition it has been found that the present solid body leads to very good results in the field of tissue engineering, where it may be used as scaffold for seeding cells onto.

The invention will now be elucidated by the following, non-restrictive examples.

EXAMPLE 1

In a beaker, 100 grams of a copolymer of polyethylene glycol terephthalate (PEGT, $M_w=1148$) and polybutylene terephthalate (PBT), wherein the weight ratio of PEGT to PBT was 60 to 40, were dissolved in 200 ml N-methylpyrrolidone (NMP) at a temperature of 100° C. by manual stirring. After approximately 30 minutes, a homogeneous solution was obtained.

The solution was allowed to cool to room temperature, upon which a gel was formed. The gel was cut from the beaker and placed in a container holding 5 liters of demineralized water. The NMP shifted from the gel into the water and a solid material was formed, which showed excellent mechanical properties in a dry state and in a wet state.

EXAMPLE 2

The procedure of example 1 was repeated, except that about 100 ml of hydroxyapatite was added to the solution before cooling to room temperature.

After placement of the gel in demineralized water, a homogeneous composite of the copolymer and hydroxyapatite was formed. The material showed excellent mechanical properties in dry and wet condition.

EXAMPLE 3

The procedure of example 1 was repeated except that about 100 ml of sodium citrate was added to the solution before cooling to room temperature.

After placement of the gel in ethanol, a polymeric matrix of the copolymer was obtained, in which matrix the sodium citrate was homogeneously distributed. The material showed excellent mechanical properties in dry and wet condition.

What is claimed is:

1. A process for molding a copolymer of a polyalkylene glycol terephthalate and an aromatic ester, comprising the steps of
    a) preparing a solution of the copolymer in a suitable first solvent; and
    b) forming a gel of the solution.
2. A process according to claim 1, wherein the first solvent is chosen from the group of N-methylpyrrolidone, 1,4-dioxane, 1,3-dioxane, and combinations thereof.
3. A process according claim 1 wherein the solution is prepared at a temperature of 20° C.–200° C.
4. A process according to claim 1, wherein the solution comprises between 5 wt. % and 90 wt. %, based on the weight of the solution, of the copolymer.
5. A process according to claim 1, wherein an additive is added to the solution, which additive is chosen from the group of calcium phosphates and biologically active agents.
6. A gel obtainable by a process according to claim 1.
7. A process according to claim 1, wherein the gel is placed in a second suitable solvent to obtain a solid body of the copolymer.
8. A process according to claim 7, wherein the second solvent is chosen from the group of water, ethanol, isopropanol, body fluids, and combinations thereof.
9. A process according to claim 7, wherein the gel is placed in an amount of at least 300 vol. %, with respect to the volume of the gel, of the second solvent.
10. A process according to claim 1, wherein the gel is freeze dried to obtain a solid body of the copolymer.
11. A solid body obtainable by a process according to the claim 7.
12. The use of a solid body according to claim 10 as a scaffold for tissue engineering or a bone filler cement.

* * * * *